US00PP11151P

United States Patent [19]

Olesen et al.

[11] Patent Number: Plant 11,151

[45] Date of Patent: Dec. 14, 1999

[54] FLORIBUNDA ROSE PLANT NAMED 'POULCHRIS'

[75] Inventors: L. Pernille Olesen; Mogens N. Olesen, both of Fredensborg, Denmark

[73] Assignee: Poulsen Roser ApS, Fredensborg, Denmark

[21] Appl. No.: 08/864,848

[22] Filed: Aug. 29, 1997

[51] Int. Cl.[6] ..... A01H 5/00

[52] U.S. Cl. ..... Plt./29

[58] Field of Search ..... Plt./28, 29

[56] References Cited

PUBLICATIONS

UPOV–ROM, 1997/06, Plant Variety Database, GTI Jouve Retrieval Software, citations for 'POULchris'.

*Primary Examiner*—Howard J. Locker

[57] ABSTRACT

A new red floribunda rose plant which has abundant non-fading flowers and good keepability. The variety successfully propagates from softwood cuttings and budding is suitable for year round production in commercial glasshouses and nurseries. This new and distinct variety has shown to be uniform and stable in the resulting generations from asexual propagation.

2 Drawing Sheets

SUMMARY OF THE INVENTION

The present invention constitutes a new and distinct variety of floribunda rose plant which originated from a controlled crossing between Christian IV and an unnamed seedling. The two parents were crossed during the summer of 1988 and the resulting seed was planted in December 1988 in a controlled environment. The new variety is named 'POULchris'.

'POULchris' was selected as a single plant from the progeny of the hybridization. The new rose may be distinguished from its seed parent, Christian IV, in that the new cultivar's flower blooms are lighter red and its growth habit more compact. The new variety may be distinguished from its pollen parent, an unnamed seedling by the same inventors, in that the pollen parent's flower blooms are soft pink in color and its growth habit is more compact than the new cultivar.

The objective of the hybridization of this rose variety for commercial greenhouse culture was to create a new and distinct variety with:

1. Uniform and abundant flowers and good repeat bloom;
2. Attractive long lasting foliage and even compact growth;
3. Year-round flowering under glasshouse and nursery conditions;
4. Suitability for production from softwood cuttings in pots; and
5. Durable flowers and foliage which make a variety suitable for distribution in the floral and nursery industry.

This combination of qualities is not present in previously available commercial cultivars of this type and distinguish 'POULchris' from all other varieties of which we are aware.

The seeds from the hybridization were germinated in 1989 and evaluations were conducted on the resulting rose plants during the winter and the spring of 1989 in a controlled environment.

'POULchris' was selected by L. Pernille and Mogens N. Olesen in their rose development program in Fredensborg, Denamrk in June, 1989.

Asexual reproduction of 'POULchris' by cuttings and traditional budding was first done by L. Pernille and Mogens N. Olesen in August, 1989. This initial and subsequent propagations have demonstrated that the characteristics of 'POULchris' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULchris'. Specifically illustrated in Sheet 1:

1. Stem showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

Specifically illustrated in Sheet 2 are buds and blooms of a flowering plant.

DETAILED DESCRIPTION OF THE VARIETY

The following is a detailed description of 'POULchris', as observed in its growth in glasshouses in Fredensborg, Denmark and Half Moon Bay, Calif. and in field nursery in Applegate, Oreg. Color references are made using The Royal Horticultural Society (London, England) Colour Chart, 1995, except where common terms of color are used.

For a comparison, the nearest existing rose variety is POULrek, a patented variety described and illustrated in U.S. Plant Pat. No. 9,688 and issued on Nov. 12, 1996. Chart 1 details several physical characteristics of 'POULchris' and 'POULrek'.

Chart 1

| | 'POULchris' | 'POULrek' |
|---|---|---|
| Upper side of petal surface | RHS 53 A of the Red Color Group | RHS 36 D of the Red Color Group |

-continued

Chart 1

| | 'POULchris' | 'POULrek' |
|---|---|---|
| Reverse side of petal surface | RHS 53 C of the Red Color Group | RHS 36 D of the Red Color Group |

Parents: Christian IV×Unnamed seedling.
Classification:
*Botanical.*—*Rosa hybrida.*
*Commercial.*—Floribunda.

FLOWER AND FLOWER BUD

Blooming cycle: Recurrent.
Flower bud:
*Size.*—20–22 mm in length when petals are just beginning to crack open.
*Bud form.*—Globular.
*Bud color.*—R.H.S. 53 C of the Red Color Group at ¼ opening.
*Sepals.*—R.H.S. 143 A of the Green Group, with streaks of red pigment on some or all. Foliaceous appendages generally not present. Surfaces of sepals pubescent.
*Peduncle.*—Surface: Hairs present. Hispid. Lenth: 35–50 mm average length. Color: R.H.S. 143 B of the Green Group, with red tones on some pedicels. Prickles: Not present.
*Receptacle.*—Surface: Glabrous, smooth. Shape: Funnel shaped. Size: Medium 7×9 mm. Color: R.H.S. 143 A of the Green Group.
*Borne.*—Singly, to 3–4 buds per stem.
Flower bloom:
*Diameter.*—Medium, 60 mm on average.
*Form.*—Upon opening, globular to square. Completely open form is flat with petals reflexing slightly. Blooms peony like, with approximately ⅓ of the flower quartered in form.
*Petalage.*—Double. Average range: 55–65. Petaloids: Present. Average range: 15–20. Length 1–2 cm. Width ½–1 cm. Color: Upper surface: Red Group 46A. Reverse surface: Red-Purple Group 58A.
*Color.*—Upon opening, the upper surface is R.H.S. 53 A of the Red Color Group. Upon opening, the reverse side is R.H.S. 53 C of the Red Color Group. After opening, the upper surface is R.H.S. 53 A of the Red Color Group. After opening, the reverse surface is R.H.S. 53 C of the Red Color Group. A small petal spot R.H.S. 4 C of the Yellow Group exists on the inner side of the petal base. A small petal spot R.H.S. 4 C of the Yellow Group exists on the outer side of the petal base.
*Reflex.*—Petals reflex backwards slightly.
*Variations.*—Exterior petals often darken at margins.
*Fragrance.*—Light fruity, apple-like scent.
*Duration.*—6–7 days as a cut flower and 8–10 days on the plant.
*Flowering stem.*—Length: On a nursery plant, 25–35 cm.
Reproductive organs:
*Pollen.*—Average. Golden yellow.
*Anthers.*—Size: Small, arranged regularly around base. Color: Yellow.
*Filaments.*—Color: Whitish green.
*Stigmas.*—Superior to anthers.
*Styles.*—Color: Whitish green.

PLANT

Plant growth: Compact and bushy. When grown as a 15–17 cm pot plant, the average height of the plant itself is 20–22 cm and the average width is 22–24 cm. When grown as a budded nursery plant, the average plant height is 45 cm and the average plant width is 36–45 cm.
Stems:
*Color.*—Young wood: R.H.S. 146 B of the Yellow Green Group. Older wood: R.H.S. 147 B of the Yellow Green Group.
*Thorns.*—Incidence: Moderately thorny. Size: Average length: 4–6 mm. Color: Red Group 51C. Shape: Concave.
*Bark.*—Young wood: Smooth. Older wood: Smooth.
Plant foliage: Normal number of leaflets on average leaves: 5 leaflets.
*Leaf size.*—Medium. 70 mm×100 mm, thick texture.
*Abundance.*—Average.
*Color, nature foliage.*—Upper leaf surface: Medium-dark green. R.H.S. 137 A of the Green Color Group, glossy. Lower leaf surface: Medium green. R.H.S. 138 B of the Green Color Group.
*Juvenile foliage.*—The upper and lower leaf surfaces are Yellow-Green Group 144A. The juvenile foliage has intonations of Greyed-Purple Group 184A.
Plant leaves and leaflets:
*Stipules.*—Present. 20–30 mm in length. Hairs present on margin. Color of mature stipules is Yellow-Green Group 144A. Juvenile stipules with marginal intonations of Greyed-Purple Group 183A.
*Rachis.*—Color: Yellow-Green Group 144A on upper surface. Yellow-Green Group 144B underneath. On juvenile foliage, rachis has intonations of Greyed-Red Group 181A.
*Petiole.*—Length: 15–20 mm. Underneath: With prickles.
*Color.*—Yellow-Green Group 144A on mature foliage. Petiole on juvenile foliage has intonations of Greyed-Red Group 181A.
*Edge.*—Finely serrated.
*Shape.*—Leaflets are broadly ovate.
*Leaflets.*—Number: 5 (most often).
Disease resistance: Resistant to mildew and rust under normal growing conditions in Half Moon Bay, Calif. and Fredensborg, Denmark.
We claim:

1. A new and distinct variety of rose plant of the floribunda class, substantially as herein illustrated and described, as a distinct and novel rose variety due to its abundant red flowers with good keepability, attractive long lasting foliage and compact growth, year round flowering under glasshouse conditions, suitability for production from softwood cuttings in pots and durable flowers and foliage which make the variety suitable for distribution in the floral industry.

* * * * *

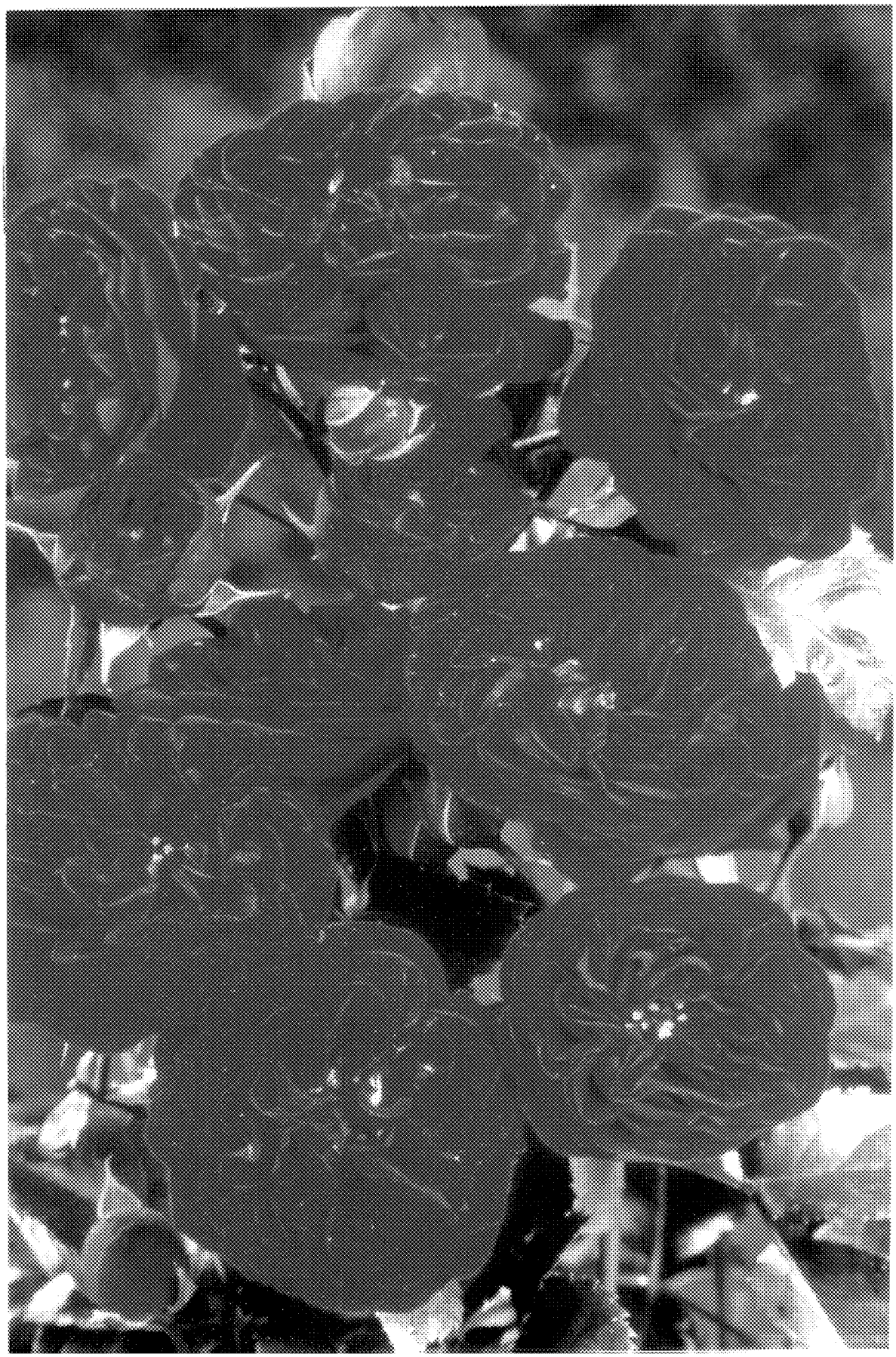

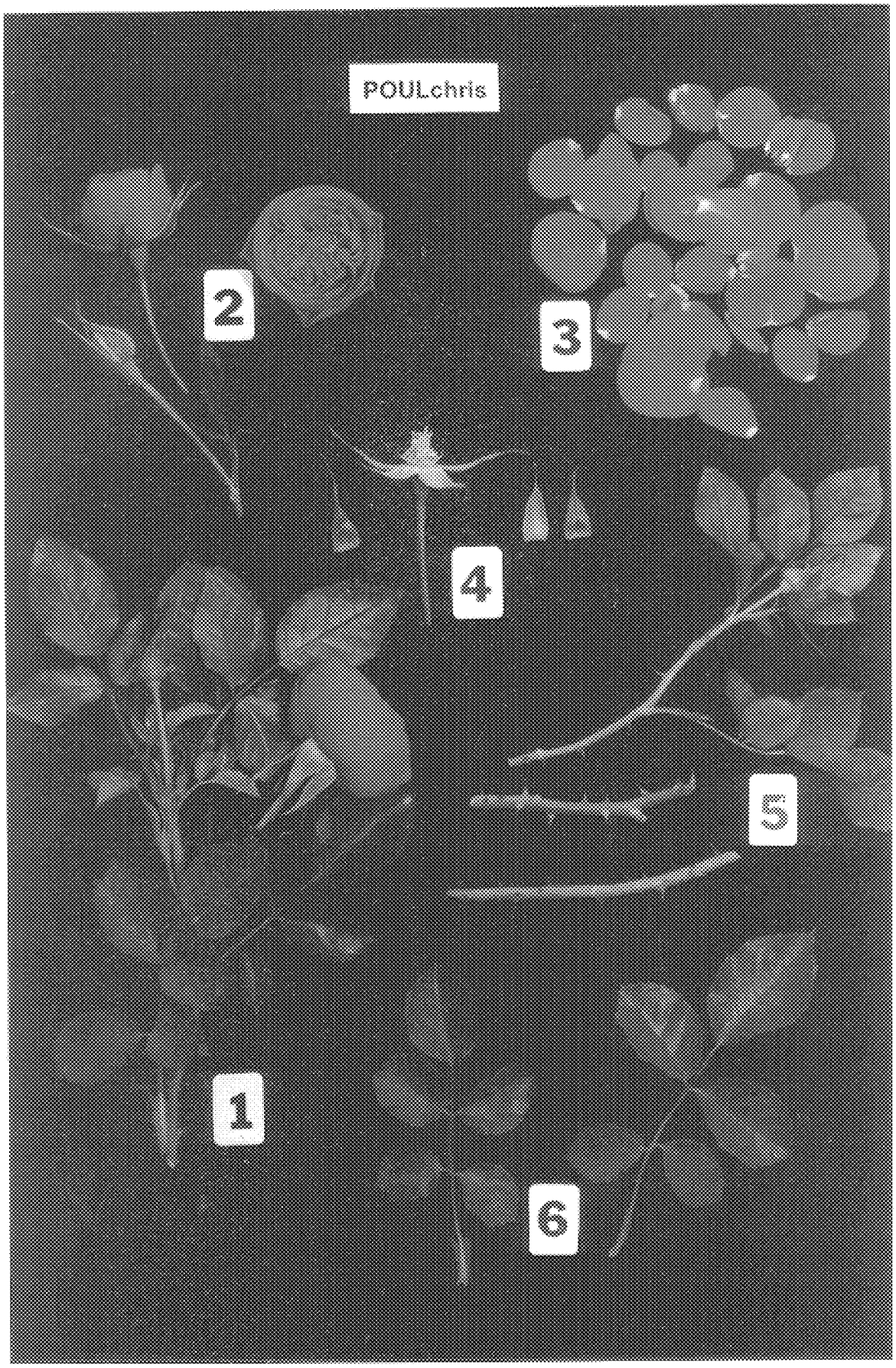
POULchris
2
3
4
5
1
6